(12) United States Patent
Mayer et al.

(10) Patent No.: US 7,241,896 B2
(45) Date of Patent: Jul. 10, 2007

(54) METHOD FOR PRODUCING 2-HALOGEN-PYRIDINE-CARBOXYLIC ACID AMIDES

(75) Inventors: Horst Mayer, Guaratingueta (BR); Dieter Golsch, Mannheim (DE); Heinz Isak, Böhl-Iggelheim (DE); Jochen Schröder, Lambsheim (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 446 days.

(21) Appl. No.: 10/494,296

(22) PCT Filed: Oct. 31, 2002

(86) PCT No.: PCT/EP02/12214

§ 371 (c)(1),
(2), (4) Date: May 3, 2004

(87) PCT Pub. No.: WO03/037868

PCT Pub. Date: May 8, 2003

(65) Prior Publication Data

US 2004/0266837 A1    Dec. 30, 2004

(30) Foreign Application Priority Data

Nov. 2, 2001    (EP) ................................. 01126113

(51) Int. Cl.
*C07D 213/46*    (2006.01)

(52) U.S. Cl. ...................................... 546/316; 546/315
(58) Field of Classification Search ................ 546/315, 546/316

See application file for complete search history.

(56) References Cited

U.S. PATENT DOCUMENTS 2,186,773 A    1/1940    Stuart
5,330,995 A    7/1994    Eicken et al.

FOREIGN PATENT DOCUMENTS

WO    WO 00/39111    *    7/2000

OTHER PUBLICATIONS

XP002189278, J.Med. Chem. 1998 41, 42288-4300, Augeri et al.

* cited by examiner

*Primary Examiner*—Zinna N. Davis
(74) *Attorney, Agent, or Firm*—Novak Druce & Quigg, LLP

(57) ABSTRACT

The invention relates to a process for preparing 2-halopyridinecarboxamides of primary aromatic monoamines I which have a substituent other than hydrogen in the ortho-position to the amino group by reaction of 2-halopyridinecarbonyl chloride II with the aromatic monoamine I, which comprises carrying out the reaction in a solvent mixture comprising water and at least one water-immiscible organic solvent in the presence of none or less than 10 mol %, based on the 2-halopyridinecarbonyl chloride II, of a base other than I or II.

10 Claims, No Drawings

METHOD FOR PRODUCING 2-HALOGEN-PYRIDINE-CARBOXYLIC ACID AMIDES

The present invention relates to a process for preparing 2-halopyridinecarboxamides, in particular 2-halonicotinamides of primary aromatic monoamines which have a substituent other than hydrogen in the ortho-position to the amino group.

2-Halopyridinecarboxamides of primary aromatic monoamines I which have a substituent other than hydrogen in the ortho-position to the amino group are known to be fungicides from EP-A 545 099. They are prepared by reacting 2-halopyridinecarbonyl chlorides with ortho-substituted aromatic monoamines in the presence of a base, preferably a tertiary amine, in an organic solvent. The base serves to bind the hydrogen halide formed in the reaction and is therefore used in at least a stoichiometric quantity. A disadvantage of this is that small base quantities remain in the initially obtained reaction product and have to be removed by complicated purification measures, in order to produce on-spec fungicide. Apart from this, the use of a base is an additional cost factor in preparing these fungicides.

There is therefore a fundamental interest in a process for preparing these fungicides which does not require the use of a base. However, it must be taken into account that ortho-substituted aromatic monoamines, referred to in the following as monoamines I, are sterically hindered because of the ortho-substituent and therefore comparatively unreactive. Additionally, the aromatic monoamines I are sufficiently basic to be protonated by the hydrogen halide formed during the reaction, so that in the absence of a base only partial conversions are generally achieved. The use of stoichiometric quantities of an auxiliary base in reacting 2-halopyridinecarbonyl chlorides II with aromatic, ortho-substituted monoamines I was accordingly hitherto regarded as necessary.

It is an object of the present invention to provide a process for preparing 2-halopyridinecarboxamides by reacting primary aromatic monoamines I with 2-halopyridinecarbonyl chlorides II which delivers the desired 2-halopyridinecarboxamides in high yield without requiring the equimolar use of a base. The process shall be especially useful for the reaction of 2-halopyridinecarbonyl chlorides with particularly unreactive aromatic monoamines of the 2-aminobiphenyl type. Additionally, the process shall also be operable on a large scale.

We have found that this object is achieved, surprisingly, by a process which involves reacting 2-halopyridinecarbonyl chloride II with an aromatic monoamine I in a solvent mixture comprising water and at least one water-immiscible organic solvent in substantial or complete absence of an auxiliary base. The high yields achieved by this process are especially surprising because pyridinecarbonyl chlorides are exceptionally prone to hydrolysis. In general, pyridinecarbonyl chlorides are therefore only converted under anhydrous conditions.

The present invention accordingly provides a process for preparing 2-halopyridinecarboxamides of primary aromatic monoamines I which have a substituent other than hydrogen in the ortho-position to the amino group by reaction of 2-halopyridinecarbonyl chloride II with the aromatic monoamine I, which comprises carrying out the reaction in a solvent mixture comprising water and at least one water-immiscible organic solvent in the presence of none or less than 10 mol %, based on the halopyridinecarbonyl chloride II, of a base other than I or II.

For the purposes of the present invention, water-immiscible organic solvents include all organic solvents and solvent mixtures which, under the hydrochloric acid reaction conditions, form a multiphasic system comprising at least one organic and at least one aqueous phase when mixed with water. In general, useful solvents are those which dissolve less than 10% by volume of water or dilute hydrochloric acid. Solvent mixtures which, in addition to the abovementioned solvents, comprise water-miscible, aprotic solvents are also useful, since these mixtures also form a biphasic system with water under the reaction conditions.

Examples of water-immiscible organic solvents include aromatic, aliphatic and cycloaliphatic hydrocarbons, aromatic, aliphatic and cycloaliphatic halogenated hydrocarbons, acyclic ethers preferably having from 4 to 10 carbon atoms, esters having from 3 to 10 carbon atoms, preferably those of aliphatic or cycloaliphatic alcohols with preferably aliphatic carboxylic acids, eg. esters of acetic acid, propionic acid or butyric acid with $C_3$-$C_8$-alkanols, such as methyl, ethyl, n-propyl, n-butyl or isobutyl acetate, propionate, butyrate, etc., and also ketones preferably having from 4 to 10 carbon atoms such as methyl ethyl ketone, and also aliphatic nitriles preferably having from 4 to 10 carbon atoms such as butyronitrile and also mixtures of the abovementioned organic solvents. Examples of useful water-miscible solvents include acetone, cyclic ethers such as tetrahydrofuran, dioxane, and also acetonitrile or propionitrile.

The contents of water-miscible solvents is in general not more than 50% by weight, preferably not more than 20% by weight, based on the total quantity of organic solvent. In a preferred embodiment, the solvent used is substantially free of water-miscible solvents (content <5% by weight).

Preference is given to such organic solvents which sufficiently dissolve at least the reactants I and II. Particular preference is given to such solvents which allow reactant concentrations of at least 20% by weight and in particular at least 30% by weight to be achieved. Examples of preferred organic solvents include aromatic, preferably alkyl-substituted hydrocarbons such as toluene, ethylbenzene, o-, m- and p-xylene, cumene and p-methylcumene, halogenated hydrocarbons, in particular chlorinated hydrocarbons such as dichloromethane, trichloromethane, 1,2-dichloroethane, chlorobenzene and dichlorobenzenes, ethers, for example $C_2$-$C_4$-dialkyl ethers such as diethyl ether, diisopropyl ether, di-n-butyl ether, di-sec-butyl ether and methyl tert-butyl ether, and also cyclic ethers such as tetrahydrofuran and metadioxane and the abovementioned esters having from 3 to 10 carbon atoms. Mixtures of the abovementioned solvents are of course also suitable. Particularly preferred solvents and solvent mixtures contain predominantly, preferably more than 80% by volume and in particular more than 90% by volume of at least one aromatic hydrocarbon. Particularly preferred aromatic hydrocarbons include $C_1$-$C_4$-monoalkyl- and $C_1$-$C_4$-dialkylbenzenes, especially xylenes.

According to the invention, the ratio of water to organic solvents is selected so that, under the reaction conditions, a first phase comprising the solvent and the reaction product, and also a second aqueous phase are formed. The quantity of water is preferably selected so that the water quantity is at least 100 g, preferably at least 200 g and in particular at least 300 g per mole of pyridinecarbonyl chloride II. In general, not more than 1 kg of water per mole of 2-halopyridinecarbonyl chloride II is used.

The quantity of water-miscible organic solvents is generally calculated so that the volume ratio of water to solvent is in the range from 10:1 to 1:10. Not least for reasons of cost, it is advantageous to keep the quantity of solvent used as small as possible. Preference is accordingly given to adding as much solvent as is necessary to make the total quantity of the reactants I and II at least 25 parts by weight, preferably at least 30 parts by weight and in particular at least 50 parts by weight, based on 100 parts by weight of the organic, water-immiscible solvent. The solvent quantity will preferably be chosen so that the reactants and also the pyridinecarboxamide will be more or less completely soluble in the organic solvent under the reaction conditions, so that a substantially homogeneous organic phase can be formed. In general, at least 100 parts by weight of solvent and preferably at least 130 parts by weight of solvent per 100 parts by weight of reactants (total quantity of I and II) will accordingly be used.

To react 2-halopyridinecarbonyl chloride II with the aromatic monoamine I, the reactants I and II are thoroughly mixed as solutions in the organic solvent in the presence of the desired quantity of water. This results in a spontaneous exothermic reaction with formation of the 2-halopyridinecarboxamide. In general, the reaction will be carried out above room temperature, but preferably above 40° C. and in particular above 50° C. Preference is given to mixing together the solutions of the reactants I and II in the organic solvent in the presence of water at a temperature above 40° C. and in particular above 50° C., for example 60 to 65° C., under quasi-adiabatic conditions, so that heating of the reactor contents occurs. In this case, "quasi-adiabatic conditions" refers to such reaction conditions under which the majority of the enthalpy released by the amide formation is not removed directly by cooling devices, but instead causes warming of the reactor contents. During the reaction, vigorous mixing is customarily effected by, for example, thorough stirring and/or circulating the reactor contents by pumping. In particular, the desired quantity of water and also the solution of the aromatic monoamine I in the desired organic solvent is initially charged to the reaction vesssel, the reactor contents heated to the desired temperature and then the solution of the 2-halopyridinecarbonyl chloride in the organic solvent introduced with mixing into the reactor. The duration of this introduction may be from a few minutes to plural hours. The preferred quasi-adiabatic method involves adding the solution of the 2-halopyridinecarbonyl chloride II preferably as quickly as possible, for example from 1 to 30 min, in particular from 1 to 15 min. The concentration of the 2-halopyridinecarbonyl chloride II in the organic solvent is generally in the range from 20 parts by weight to 200 parts by weight per 100 parts by weight of organic solvent.

After the addition has ended, the components are generally allowed to react further for a period of time, preferably not more than 1 h, before the workup is begun. This further reaction is preferably effected with mixing of the reactor contents.

The workup is effected by customary aqueous extractive methods. To this end, the aqueous phase is generally first removed from the possibly still hot reaction mixture. The organic phase is then neutralized, optionally after thinning with further organic solvent, by addition of an aqueous solution of an inorganic base. Examples of useful bases include alkali metal hydroxides such as sodium hydroxide or potassium hydroxide, alkali metal carbonates and hydrogen carbonates and in particular sodium carbonate. The neutralization may be effected in one or more steps. The neutralization preferably involves setting a pH in the range from 6 to 10 and in particular in the range from 7 to 9. The neutralization procedure is preferably likewise effected at temperatures above 40° C., in particular above 60° C., and particularly above 85° C., for example in the range from 60 to 100° C. or in the range from 85 to 100° C. Preference is given to adding a hot aqueous base solution to the hot organic phase. The neutralization may take place in one or more steps, and after each step, the aqueous phase is removed from the organic phase.

The recovery of further quantities of fungicide will generally be achieved by reextracting the first aqueous phase or the combined aqueous phases with the organic solvent and neutralizing the obtained organic solution, optionally in the above-described manner. Preference is given to returning the thus recovered re-extract to the reaction, for example to a subsequent batch. Of course, the fungicide may also be isolated from the re-extract.

The isolation of the 2-halopyridinecarboxamide prepared in this way from the organic phase is effected in a customary manner, for example by concentration and/or cooling of the organic solutions and crystallization. The crystallization may be carried out, for example, in the presence of seed crystals.

To prepare the 2-halopyridinecarboxamide, the reactants I and II are used in near stoichiometric quantities, ie. the molar ratio of 2-halonicotinyl chloride II and aromatic amine I is in the range from 0.9:1 to 1:1.1. However, preference is given to using the 2-halonicotinyl chloride II in at least an equimolar quantity or in a small excess of up to 10 mol %, preferably up to 5 mol %, based on I.

According to the invention, the process enables all primary aromatic monoamines II which have a substituent other than hydrogen in the ortho-position to the amino group to be converted. In principle, useful substituents are those which are inert under the given reaction conditions, ie. do not enter into competing reaction with the acid chloride function of 2-halopyridinecarbonyl chloride II. Examples of such substituents include halogen, nitro, cyano, alkyl, haloalkyl, cycloalkyl, alkoxy, alkoxyalkyl, alkylthio, alkylsulfonyl, aryl, heteroaryl, arylalkyl and heteroarylalkyl. The aryl and heteroaryl groups of the last four radicals mentioned may themselves have 1, 2 or 3 of the groups mentioned as substituents, for example halogen, nitro, cyano, alkyl, haloalkyl, alkoxy, alkoxyalkyl, alkylthio, alkylsulfonyl, aryl and/or cycloalkyl. In addition to the substituents in the ortho-position to the amino group, the aromatic monoamine may also carry further, for example 1 or 2, further substituents of the abovementioned type. Two substituents bonded to neighboring carbon atoms of the aromatic combined may also form a carbocyclic or heterocyclic 5- or 6-membered ring which may itself be substituted, for example, by halogen or alkyl.

The aromatic monoamines are preferably derived from aniline. However, amines of polycyclic aromatics such as naphthylamines or amines of benzoheterocycles may also be used as the monoamine I. The aromatic monoamines, in particular the aniline compounds, may of course in addition to the substituent in the ortho-position also have further, for example 1 or 2, substituents of the abovementioned type. In a preferred embodiment of the present invention, an aniline which is only substituted in the ortho-position is used.

For the purposes of the present invention, alkyl is a linear or branched saturated hydrocarbon radical preferably having from 1 to 6 and in particular from 1 to 4 carbon atoms, such as methyl, ethyl, n-propyl, isopropyl, n-butyl, 2-butyl, isobutyl and tert-butyl. The same applies to the alkyl moieties in alkoxy, alkythio, alkoxyalkyl and alkylsulfonyl.

For the purposes of the present invention, haloalkyl is a partially or completely halogen-, in particular fluorine-, chlorine-, bromine- or iodine-substituted, linear or branched, saturated hydrocarbon radical having preferably from 1 to 4 carbon atoms, for example chloromethyl, dichloromethyl, trichloromethyl, fluoromethyl, difluoromethyl, chlorodifluoromethyl, dichlorofluoromethyl, trifluoromethyl, bromomethyl, 2,2,2-trichloroethyl, 2,2,2-trifluoromethyl, 2-chloroethyl, pentafluoroethyl, pentachloroethyl, 3-chloropropyl, 3-bromopropyl, etc.

Alkoxyalkyl is a linear or branched alkyl radical which is substituted by a $C_1$-$C_4$-alkoxy group, for example methoxymethyl, ethoxymethyl, n- or i-propoxymethyl, n-butoxymethyl, 1-methoxyethyl, 1-ethoxyethyl, 2-methoxyethyl, 2-ethoxyethyl, etc.

Cycloalkyl is a mono- or bicyclic hydrocarbon radical which generally has from 3 to 10 carbon atoms, such as cyclopropyl, cyclopentyl, cyclohexyl, norbornyl, decalinyl or adamantyl.

Aryl is preferably phenyl or naphthyl, each of which may be substituted by 1, 2 or 3 of the abovementioned substituents.

Heteroaryl is a heteroaromatic radical which may be mono- or bicyclic and has from 1 to 3 heteroatoms selected from O, N and S, although none of the heteroatoms may be protonatable in the aqueous phase. Examples of hetaryl are in particular thienyl, furanyl, benzothienyl, indolyl and the like. Aryl and hetaryl may be substituted by one or more, for example 1, 2 or 3, of the abovementioned substituents.

In a particularly preferred embodiment of the present invention, a primary aromatic monoamine I is used which has, in the ortho-position to the amino group, a phenyl substituent which may itself be substituted, for example by 1, 2 or 3 of the abovementioned substituents. In particular, the present invention relates to a process where the aromatic monoamine I used is an aniline compound which has an optionally substituted phenyl ring in the ortho-position to the amino group, ie. an aromatic monoamine I of the 2-aminobiphenyl type. The phenyl ring may be substituted as described above and preferably has 1, 2 or 3 of the abovementioned substituents. Particularly preferred substituents are selected from halogen, methyl, difluoromethyl, trifluoromethyl, methoxy, methylthio or methylsulfonyl. In a special embodiment of the present invention, the aromatic monoamine I used is a 2-(halophenyl)aniline, for example 2-(4-chlorophenyl)aniline or 2-(4-fluorophenyl)aniline.

The 2-halopyridinecarbonyl chlorides used in the process according to the invention are preferably 2-halonicotinyl chlorides and in particular 2-chloronicotinyl chloride (=2-chloro-3-pyridinecarbonyl chloride).

The process according to the invention delivers 2-halopyridinecarboxamides of sterically hindered, primary aromatic monoamines I which have a substituent other than hydrogen in the ortho-position to the amino group in high yields without requiring the use of a base. The yields from conventional workup are generally above 80% of the theoretical yield. Re-extraction of the aqueous phase regularly enables the yield to be increased above 90%. Surprisingly, only a very small quantity of 2-hydroxynicotinamide, which customarily results from acid hydrolysis of 2-halonicotinamides, is formed under the reaction conditions.

The present invention is illustrated by the following example:

Preparation of 2-chloro-[2-(4-chlorophenyl)phenylaminocarbonyl]pyridine by reaction of 2-chloro-3-nicotinyl chloride II with 2-(4-chlorophenyl)aniline I

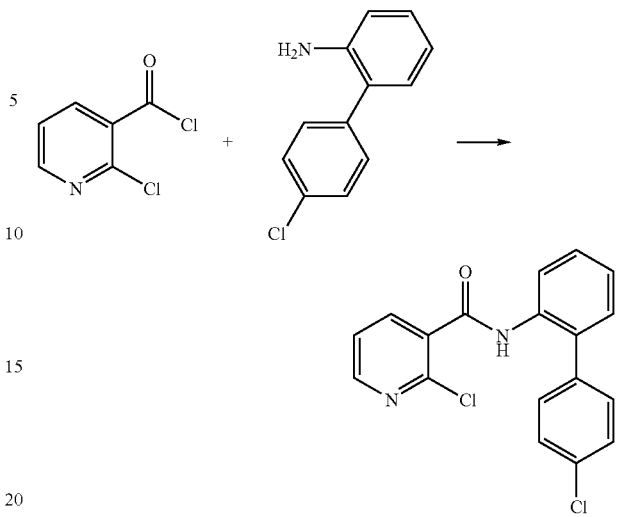

A reaction vessel was charged with 800 g of water and a solution of 396 g (1.944 mol) of 2-amino-4'-chlorobiphenyl in 311 g of xylene and heated with stirring to an internal temperature of 65° C. A solution of 349 g (1.984 mol) of 2-chloro-3-nicotinyl chloride in 233 g of xylene which had been heated to 65° C. was then added. This resulted in a temperature increase in the reaction vessel to about 95° C. After the addition had ended, the temperature was maintained for a further 10 minutes with stirring, then the stirrer was switched off and the phases allowed to separate. The aqueous phase was run off and collected. About 360 g of hot water were added to the organic phase, which was then stirred and a first portion of a 20% by weight aqueous sodium carbonate solution was added. The aqueous phase was then separated off and 360 g of hot water and further 20% by weight sodium carbonate solution were then added to the organic phase. After separating off the aqueous phase, the hot organic phase was transferred to a preheated reservoir. It was then cooled with stirring to room temperature and the title compound crystallized out. After separating off the mother liquor and drying the crystals, 567 g of the fungicide were obtained. This corresponds to a yield of 85% based on the 2-aminobiphenyl used.

Re-extraction of the aqueous phases with xylene delivered a further 53 g of the title compound. The total yield was 620 g (93% of the theoretical yield).

We claim:

1. A process for preparing 2-halopyridinecarboxamides of primary aromatic monoamines I which have a substituent other than hydrogen in the ortho-position to the amino group by reaction of 2-halopyridinecarbonyl chloride II with the aromatic monoamine I, which comprises carrying out the reaction in a solvent mixture comprising water and at least one water-immiscible organic solvent in the presence of none or less than 10 mol %, based on the 2-halopyridinecarbonyl chloride II, of a base other than I or II.

2. A process as claimed in claim 1, wherein the water quantity is at least 100 g per mole of 2-halopyridinecarbonyl chloride II.

3. A process as claimed in claim 1, wherein the total quantity of compounds I and II is from 25 parts by weight to 100 parts by weight, based on 100 parts by weight of organic solvent.

4. A process as claimed in claim 1, wherein the organic solvent is selected from aromatic hydrocarbons, halogenated hydrocarbons, ethers, esters having from 3 to 10 carbon atoms and mixtures thereof.

5. A process as claimed in claim 1, wherein the reaction is carried out at temperatures above 40° C.

6. A process as claimed in claim 1, wherein the reaction is carried out in the absence of a base other than I or II.

7. A process as claimed in claim 1, wherein the 2-halopyridinecarbonyl chloride II and the aromatic amine I are reacted in a molar ratio of from 1:1.1 to 1:1.

8. A process as claimed in claim 1, wherein the substituent in the ortho-position of the amino group in I is a phenyl group which is optionally substituted by 1, 2 or 3 substituents selected from the crroup consisting of: halogen, nitro, cyano, alkyl, haloalkyl, alkoxy, alkoxyalkyl, alkyithio, alkylsulfonyl, aryl and cycloalkyl.

9. A process as claimed in claim 8, wherein the aromatic amine I is selected from 2-(halophenyl)anilines.

10. A process as claimed in claim 1, wherein compound II is 2-chioropyridinecarbonyl chloride.

* * * * *